United States Patent [19]

Hunter et al.

[11] 4,282,428

[45] Aug. 4, 1981

[54] CHROMOSOME DETECTOR USING A SCANNING MICROSCOPE SYSTEM

[75] Inventors: Gerald D. Hunter, Lino Lakes, Minn.; Gaston A. Palombo, Agoura, Calif.

[73] Assignee: Honeywell Inc., Minneapolis, Minn.

[21] Appl. No.: 85,745

[22] Filed: Oct. 17, 1979

[51] Int. Cl.³ ............................................. G01J 1/20
[52] U.S. Cl. ............................................. 250/214 R
[58] Field of Search ................... 250/201, 214 R, 550, 250/310, 311; 356/39

[56] References Cited

U.S. PATENT DOCUMENTS 4,000,417 12/1976 Adkisson et al. ................... 25/201

Primary Examiner—David C. Nelms
Assistant Examiner—Darwin R. Hostetter
Attorney, Agent, or Firm—Laurence J. Marhoefer; Lockwood D. Burton; Mitchell J. Halista

[57] ABSTRACT

A chromosome detector using a scanning microscope system is used to detect the presence of a chromosome spread in a slide specimen and to produce a signal usable by the scanning microscope system to automatically operate the microscope system whereby the detected chromosomes are centered in the field of view, are automatically focused and their location converted to coordinate data which is stored in a memory system whereby the system may be used to re-examine the detected chromosome by the use of the stored X-Y coordinates. The detector performs an amplitude and frequency analysis of a cell find signal produced by a slide scanner in the scanning microscope system and produces, in turn, an output signal representative of a detected chromosome spread and compatible with the scanning microscope control circuit.

5 Claims, 3 Drawing Figures

CHROMOSOME DETECTOR USING A SCANNING MICROSCOPE SYSTEM

BACKGROUND OF THE INVENTION

1. Field of the Invention

The present invention relates to the field of scanning microscope systems. More specifically, the present invention is directed to a chromosome detector for a scanning microscope system.

2. Description of the Prior Art

Scanning microscope systems for locating and counting leukocytes and red blood cells on prepared slides are well-known in the art as found in U.S. Pat. No. 4,000,417. Another automatic microscope scanning system is shown in U.S. Pat. No. 4,082,457 using color detection for determining the presence of blood cells. However, neither of these prior art systems are useful for the automatic detection of chromosome spreads for karyotyping inasmuch as the criteria used to detect red and white blood cells is ineffective in accurately determining the presence of chromosome spreads in conventional media, e.g., amniotic fluid, pleural effusion, etc. Accordingly, it is desirable to provide an improved scanning microscope system having a chromosome detector for automatically detecting the presence of chromosome spreads in a specimen under analysis.

SUMMARY OF THE INVENTION

An object of the present invention is to provide an improved scanning microscope system having a chromosome detector.

In accomplishing this and other objects, there has been provided, in accordance with the present invention, a chromosome detector for a scanning microscope system for analyzing a cell find output signal from the scanner used in the scanning microscope system which is obtained during the scanning of a sample to be analyzed by performing an amplitude and frequency analysis on the scanner output signal to determine the presence of a chromosome spread. The analysis ultimately produces a control signal suitable for controlling the scanning microscope system to achieve a recognition of the presence of the chromosome spread and a storage of the X-Y coordinates representing the location of the chromosome spread.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

DETAILED DESCRIPTION

Figure 1:
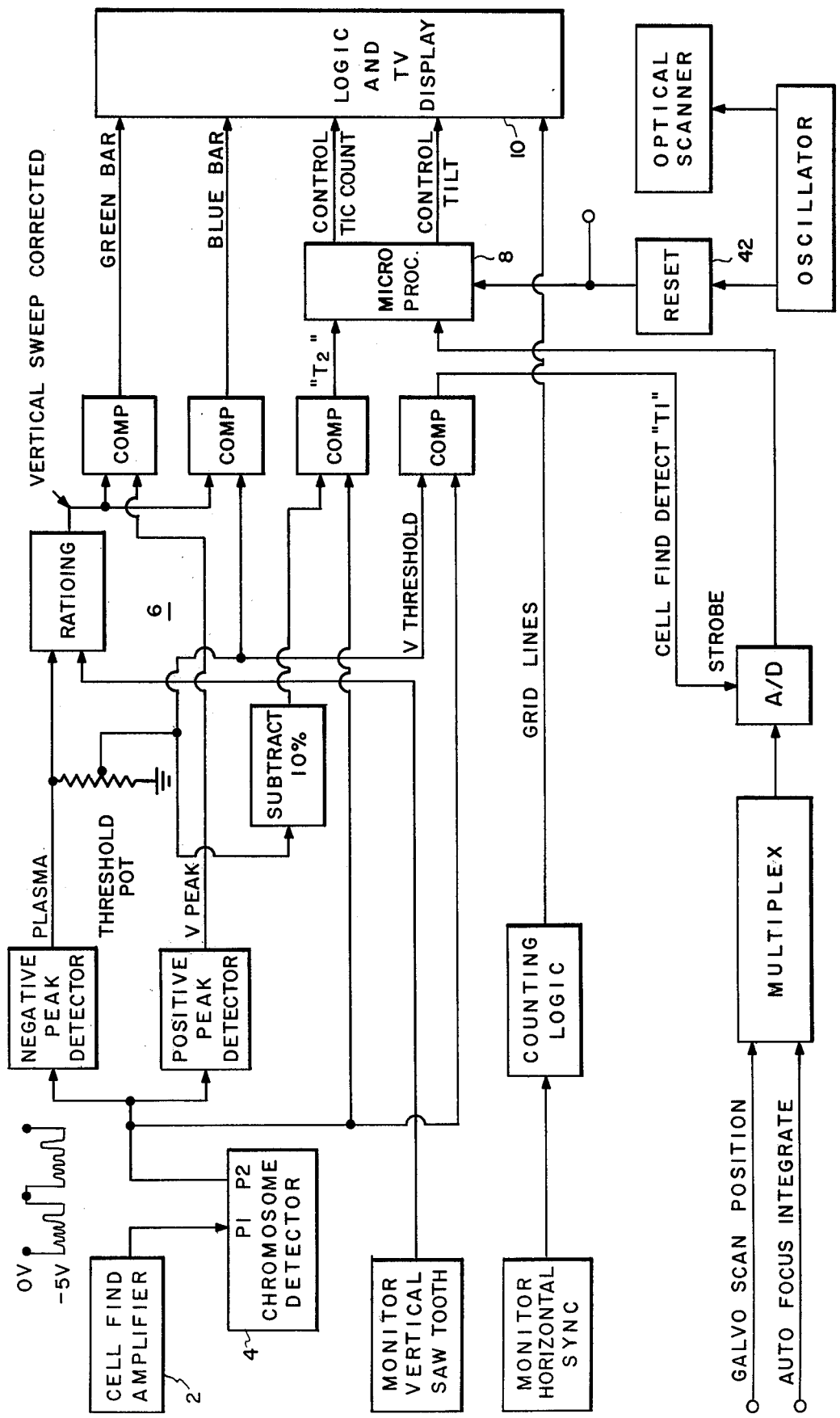
FIG. 1 is a simplified block diagram of a conventional scanning microscope system.

Referring to FIG. 1 in more detail, there is shown a block diagram of the conventional scanning microscope system and specifically a simplified representation of the scanning microscope system shown in U.S. Pat. No. 4,000,417 and sold as the ACS 1000 Scanning Microscope by Honeywell Inc., Minneapolis, Minn. This system includes a means for scanning the prepared slide on which the cells to be analyzed are located which scanning means includes an X-Y-Z drive system for the slide as well as an optical galvanometer drive means for sequentially scanning preselected incremental areas of the slide to develop a cell find signal therefrom through a cell find amplifier 2. The conventional operation of the aforesaid scanning microscope performs an amplitude analysis on the output signal from the cell find amplifier to enable the system to discriminate between the desired sample cells and undesired sample components. In this prior art system, chromosome spreads are not identified since only large amplitude changes of the cell find signal corresponding to a dark cell nucleus are recognized, and the chromosome spreads are rejected as undesired elements.

A chromosome detector 4 is used in the present invention to perform an amplitude and frequency analysis of the cell find signal and to produce an output signal representative of a chromosome spread in a format identifiable by the scanning microscope system as a proper cell find signal. On the other hand, the chromosome detector 4 rejects blood cells and other miscellaneous sample items by providing a corresponding output signal to the scanning microscope system which is rejected as a proper cell find signal. Thus, the cell find signal is applied through the chromosome detector 4 to produce an output signal indicative of the presence of the chromosome spread in the form of a signal suitable for use with the conventional scanning microscope system as shown in the aforesaid U.S. Pat. No. 4,000,417.

That scanning microscope system uses the signal from the chromosome detector 4 in an amplitude analysis circuit 6 to produce an output indicative of the presence of the desired item under study, i.e., chromosome spreads, and to store in a microprocessor 8 the X—Y coordinates of the location of the chromosome spread for subsequent analysis on a television display 10. Further discussion of this conventional scanning microscope system is believed to be unnecessary in order to provide a complete understanding of the present invention since that scanning microscope system with the exception of the chromosome detector 4 operates in the manner as discussed in U.S. Pat. No. 4,000,417 and as embodied in the ACS 1000 Scanning Microscope product.

Figure 2:
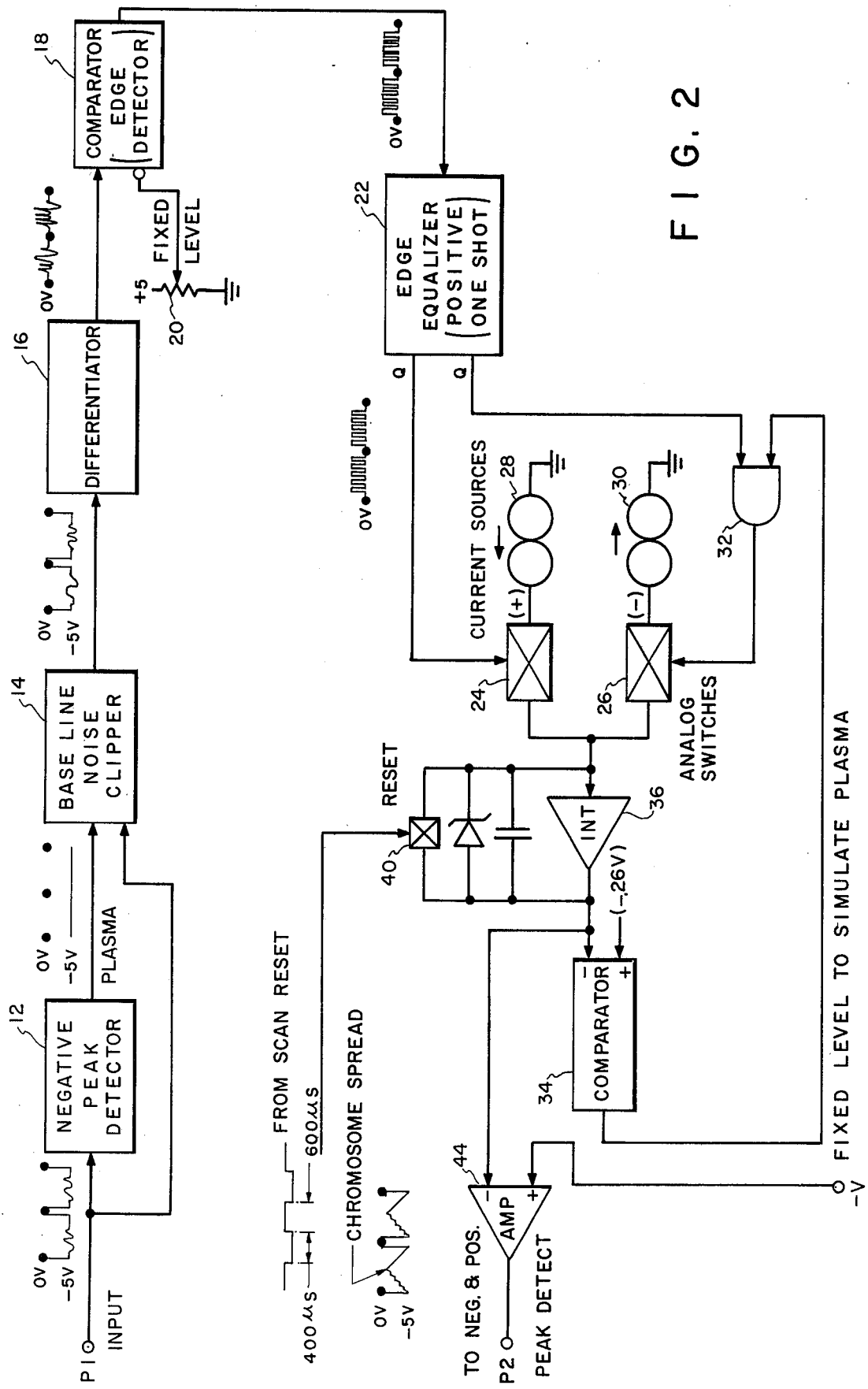
FIG. 2 is a block diagram of a chromosome detector circuit embodying an example of the present invention for use with the scanning microscope system shown in FIG. 1

Referring to FIG. 2, there is shown a block diagram of a novel chromosome detector circuit embodying an example of the present invention for use as the chromosome detector 4 shown in the scanning microscope system in FIG. 1. The waveshapes occurring at the inputs to the various circuits are illustrated in FIG. 2 for the purpose of assisting the following description of the operation of the chromosome detector circuit. The chromosome detector 4 operates on the cell find signal from cell find amplifier 2 to perform an amplitude and frequency analysis to produce an output signal representative of a chromosome spread which output signal is acceptable to the scanning microscope system. The input signal from the cell find amplifier 2 is applied to a negative peak detector 12 and to a baseline noise clipper 14. The negative peak detector 12 is effective to produce peak pulses representative of the peaks of the input signal to the peak detector. The baseline noise clipper 14 combines these detected peaks with the overall cell find signal envelope to produce an output waveshape having a reproduction of the signal envelope but with emphasized signal peaks. This waveshape is subsequently applied to a differentiator 16 wherein the signal envelope which was displaced from a zero baseline is converted to a signal envelope about a common, or zero, baseline.

The output from the differentiator 16 is applied to a signal comparator 18, or edge detector, for comparing the signal with a fixed level signal derived from a potentiometer 20. The comparator 18 is effective to remove any negative excursions and to produce squarewave representations of the remaining signals. The output of the comparator 18 is applied to an edge equalizier 22 which uses a positive single shot, or astable multivibrator, to produce standardized pulses between the peak signal points. The Q and $\overline{Q}$ outputs from the equalizier 22 are applied to analog switches 24, 26 to control the outputs from respective current sources 28, 30. Specifically, the Q output of the equalizier 22 is applied directly to the current switch 24 while the $\overline{Q}$ output of the equalizier 22 is applied through a two input NAND gate 32 to control the analog switch 26.

The other input for the NAND gate 32 is obtained from a signal comparator circuit 34 as hereinafter described. The analog switches 24 and 26 are used to control the current supplied to an integrator circuit 36. The integrator circuit 36 has a reset switch 40 which is reset by an output signal from a reset circuit 42 shown in the scanning microscope block diagram of FIG. 2. The output signal from the integrator 36 is applied to the comparator 34 to be compared with a fixed level signal and to an output amplifier 44. The output from the amplifier 44 is applied in the block diagram of the scanning microscope system shown in FIG. 1 as the output from the chromosome detector 4.

Thus, the chromosome detector circuit shown in FIG. 2 performs an amplitude analysis on the cell find signal after the signal has been modified by the signal shaping circuits 12, 14, and 16 and subsequently performs a frequency analysis by means of the integrator 36 to produce an output signal dependent on the number of signals applied to the integrator before the reset operation. Thus, the output signal from the integrator 36 is effective to reach a signal level suitable for operating the scanning microscope system shown in FIG. 1 when a chromosome spread has been actually detected. The detection of a chromosome spread, i.e., a plurality of chromosomes, is based on the novel use of the plurality of pulses from the cell find amplifier 2 which are occasioned by the presence of a plurality of chromosomes in an incremental scan area. As a result, the chromosome detector 4 differentiates between the plurality of chromosomes in a chromosome spread and a single cell producing a cell find signal pulse since the single cell pulse will not pass the frequency test to produce a suitable output signal from the integrator 36. Thus, while the ACS 1000 scanning microscope performs an amplitude analysis to detect individual red and white blood cells, it is the unique combination of an amplitude and frequency analysis that produces the chromosome detection of the present invention. The scanning microscope system of FIG. 1, subsequently uses the chromosome detector output signal to operate its detection and coordinate storage circuits as discussed above and as found in U.S. Pat. No. 4,000,417.

Figure 3:
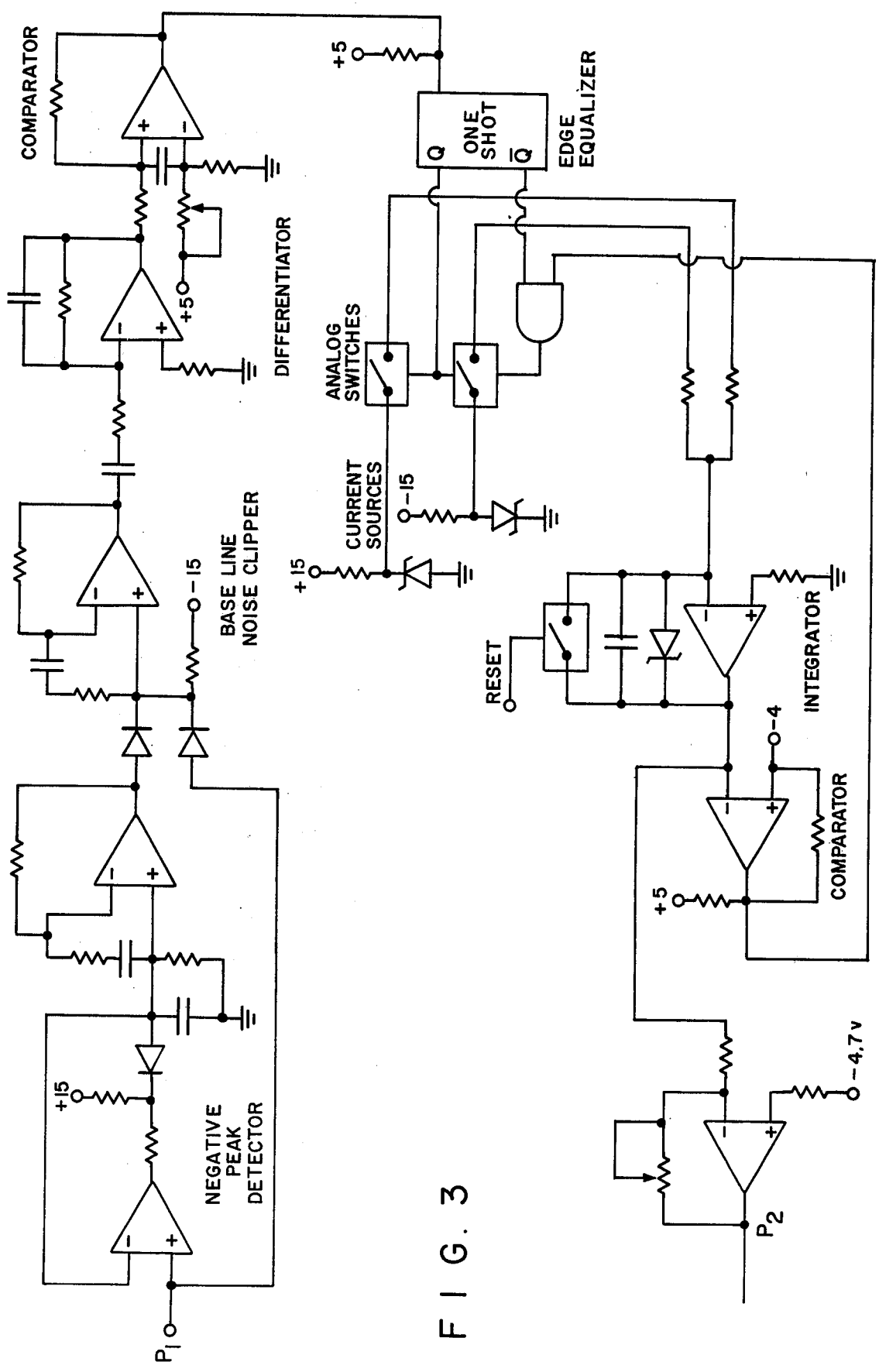
FIG. 3 is a schematic diagram of a circuit suitable for the chromosome detector shown in FIG. 2.

A circuit suitable for use as the chromosome detector shown in FIG. 2 is shown in FIG. 3 with the component circuits identified to correspond with those shown in FIG. 2. A further detailed discussion of this circuit is believed to be unnecessary inasmuch as the individual component circuits shown therein are conventional and the operation thereof is well-known.

Accordingly, there is shown that there been provided, in accordance with the present invention a chromosome detector for use with a scanning microscope to produce an indication of the location of chromosome spreads.

The embodiments of the invention in which an exclusive property or privilege is claimed are defined as follows:

1. A chromosome detector comprising:
    input means for producing a signal representative of a scan of a predetermined incremental area of a prepared slide,
    amplitude analyzing means for analyzing the amplitude of said signal with respect to a threshold level and
    frequency analyzing means for analyzing the output of said amplitude analyzing means to produce an output signal having a frequency dependent amplitude.

2. A chromosome detector as set forth in claim 1 wherein said frequency analyzing means includes an integrator circuit for integrating an output signal from said amplitude analyzing means.

3. A method of operating a scanning microscope system including the steps of performing an amplitude analysis on a cell find signal, and subsequently performing a frequency analysis of the output from the amplitude analysis to produce an output signal representative of a desired element of the cell find signal and suitable for use by the scanning microscope system.

4. In combination with a scanning microscope system having means for scanning a prepared slide to produce a cell find signal and means responsive to the cell find signal for determining the presence of a desired element on the prepared slide to produce X-Y coordinates of the location of the desired element on the slide, the improvement comprising:
    an amplitude analysis means for performing an amplitude analysis on said cell find signal and
    a frequency analysis means for performing a frequency analysis on an output from said amplitude analysis circuit to produce an output signal upon the occurrence of a desired element in the scanned sample, said output signal being suitable for use as a cell find signal by the scanning microscope system.

5. A combination as set forth in claim 4 wherein said frequency analysis means includes an integrator for integrating said output signal from said amplitude analysis means.

* * * * *